(12) United States Patent
English et al.

(10) Patent No.: US 12,702,844 B2
(45) Date of Patent: Aug. 11, 2026

(54) HEADER COMPOSITE BORE FOR REDUCED LEAD INSERTION FORCE

(71) Applicant: Cardiac Pacemakers, Inc., St. Paul, MN (US)

(72) Inventors: James Michael English, Cahir (IE); Moira B. Sweeney, St. Paul, MN (US); Robert Allen Jones, Lake Elmo, MN (US); Benjamin J. Haasl, Forest Lake, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 265 days.

(21) Appl. No.: 18/398,448

(22) Filed: Dec. 28, 2023

(65) Prior Publication Data

US 2024/0216700 A1 Jul. 4, 2024

Related U.S. Application Data

(60) Provisional application No. 63/435,885, filed on Dec. 29, 2022.

(51) Int. Cl.
*A61N 1/375* (2006.01)

(52) U.S. Cl.
CPC ....... *A61N 1/37512* (2017.08); *A61N 1/3752* (2013.01)

(58) Field of Classification Search
None
See application file for complete search history.

(56) References Cited

U.S. PATENT DOCUMENTS

2020/0376281 A1* 12/2020 Dweck .................. A61N 1/375
2021/0187306 A1 6/2021 Spadgenske et al.
2022/0047876 A1 2/2022 Becklund et al.

* cited by examiner

*Primary Examiner* — Carl H Layno
*Assistant Examiner* — Bryan Mcallister Lee
(74) *Attorney, Agent, or Firm* — Nelson Mullins Riley & Scarborough LLP

(57) ABSTRACT

An implantable medical device can include a housing including electronic devices within the housing; a header attached to the housing and including one or more bores configured to receive a lead; and wherein one of the bores includes a structure wherein a first section of the bore includes walls having a relatively lower coefficient of friction compared to walls of the bore at a closed tip end section of the bore.

20 Claims, 4 Drawing Sheets

114
230
119
212
210
119
222
220

114
230
310
212
210
221
220

HEADER COMPOSITE BORE FOR REDUCED LEAD INSERTION FORCE

CLAIM OF PRIORITY

This application claims the benefit of U.S. Provisional Application No. 63/435,885 filed on Dec. 29, 2022, which is hereby incorporated by reference in its entirety.

TECHNICAL FIELD

Various embodiments described herein relate to apparatus, systems, and methods associated with implantable medical devices.

BACKGROUND

An ambulatory medical device, such as an implantable medical device (IMD), can be configured for implant in a subject, such as a patient. An IMD can be configured to be coupled to a patient's heart such as via one or more implantable leads. Such an IMD can obtain diagnostic information or generate therapy to be provided to the patient, such as via the coupled implantable lead.

In one configuration, IMDs have a header that is coupled to a container that houses much of the electronics of the IMD. The header can include a bore to receive the lead and couple the lead with circuitry within the implantable device. However, the insertion of a lead into the bore can require a large force.

SUMMARY

Example 1 can include subject matter such as an implantable device. An implantable medical device can include a housing including electronic devices within the housing; a header attached to the housing and including one or more bores configured to receive a lead; and wherein one of the bores includes a structure wherein a first section of the bore includes walls having a relatively lower coefficient of friction compared to walls of the bore at a closed tip end section of the bore.

In Example 2, the subject matter of Example 1 can optionally include the walls of the first section of the bore including an additive to a substrate material of the bore to provide the lower coefficient of friction.

In Example 3, the subject matter of any one or more of Examples 1-2 can optionally include the walls of the first section being opaque and the walls of the closed tip end section being clear such that a user can see a lead within the closed tip end section of the bore.

In Example 4, the subject matter of any one or more of Examples 1-3 can optionally include the header including a clear plastic.

In Example 5, the subject matter of any one or more of Examples 1-4 can optionally include the entire bore being formed of the same clear substrate with an additive being added to the substrate only in the first section to make the first section have a lower coefficient of friction than the clear substrate.

In Example 6, the subject matter of any one or more of Examples 1-5 can optionally include there being no seals within the bore.

In Example 7, the subject matter of any one or more of Examples 1-6 can optionally include the bore being configured to receive an IS-1 or DF-1 type implantable lead.

In Example 8, the subject matter of any one or more of Examples 1-7 can optionally include the bore including an electrical contact to contact a lead.

In Example 9, the subject matter of any one or more of Examples 1-8 can optionally include the first section extending from a bore opening to a beginning of the closed tip end section.

In Example 10, the subject matter of any one or more of Examples 1-9 can optionally include a non-migrating lubricant located on the wall of the first section of the bore.

In Example 11, the subject matter of any one or more of Examples 1-10 can optionally include the non-migrating lubricant having lower coefficient of friction than a substrate of the bore.

Example 12 can include subject matter including a method for inserting a lead into a header, the method can include inserting a lead into a bore wherein the lead first goes through a first section of the bore having a lower coefficient of friction than a closed tip end section of the bore; inserting the lead farther into the bore such that a proximal tip of the lead enters the closed tip end section; and visually seeing the proximal tip of the lead within the closed tip end section.

In Example 13, the subject matter of any one or more of Examples 1-12 can optionally include the bore including a composite structure wherein the first section of the bore includes walls having a relatively lower coefficient of friction compared to walls of the bore at the closed tip end section of the bore.

In Example 14, the subject matter of any one or more of Examples 1-13 can optionally include the walls of the first section of the bore including an additive to a substrate material of the bore to provide the lower coefficient of friction.

In Example 15, the subject matter of any one or more of Examples 1-14 can optionally include the walls of the first section being opaque and the walls of the closed tip end section being clear such that a user can see a lead within the closed tip end section of the bore, and wherein the header is overmolded with a clear plastic.

In Example 16, the subject matter of any one or more of Examples 1-15 can optionally include a non-migrating lubricant located on walls of the first section of the bore.

Example 17 can include subject matter including a method of manufacturing a header for an implantable device, the method can include forming a bore wherein the bore includes a structure wherein a first section of the bore includes walls having a relatively lower coefficient of friction compared to walls of the bore at a closed tip end section of the bore; and overmolding the bore to form a header.

In Example 18, the subject matter of any one or more of Examples 1-17 can optionally include the walls of the first section of the bore including an additive to a substrate material of the bore to provide the lower coefficient of friction, wherein the walls of the first section are opaque and the walls of the closed tip end section are clear such that a user can see a lead within the closed tip end section of the bore.

In Example 19, the subject matter of any one or more of Examples 1-18 can optionally include the header being overmolded with a clear plastic.

In Example 20, the subject matter of any one or more of Examples 1-19 can optionally include applying a non-migrating lubricant on the walls of the first section of the bore.

In Example 21, subject matter (e.g., a system or apparatus) may optionally combine any portion or combination of any portion of any one or more of Examples 1-20 to comprise "means for" performing any portion of any one or more of the functions or methods of Examples 1-20, or at least one "non-transitory machine-readable medium" including instructions that, when performed by a machine, cause the machine to perform any portion of any one or more of the functions or methods of Examples 1-20.

This summary is intended to provide an overview of subject matter of the present patent application. It is not intended to provide an exclusive or exhaustive explanation of the disclosure. The detailed description is included to provide further information about the present patent application. Other aspects of the disclosure will be apparent to persons skilled in the art upon reading and understanding the following detailed description and viewing the drawings that form a part thereof, each of which are not to be taken in a limiting sense.

DETAILED DESCRIPTION

In the following detailed description, reference is made to the accompanying drawings that form a part hereof and in which are shown, by way of illustration, specific embodiments in which the invention may be practiced. These embodiments are described in sufficient detail to enable those skilled in the art to practice the invention. Other embodiments may be utilized and structural, logical, and electrical changes may be made.

Figure 1:
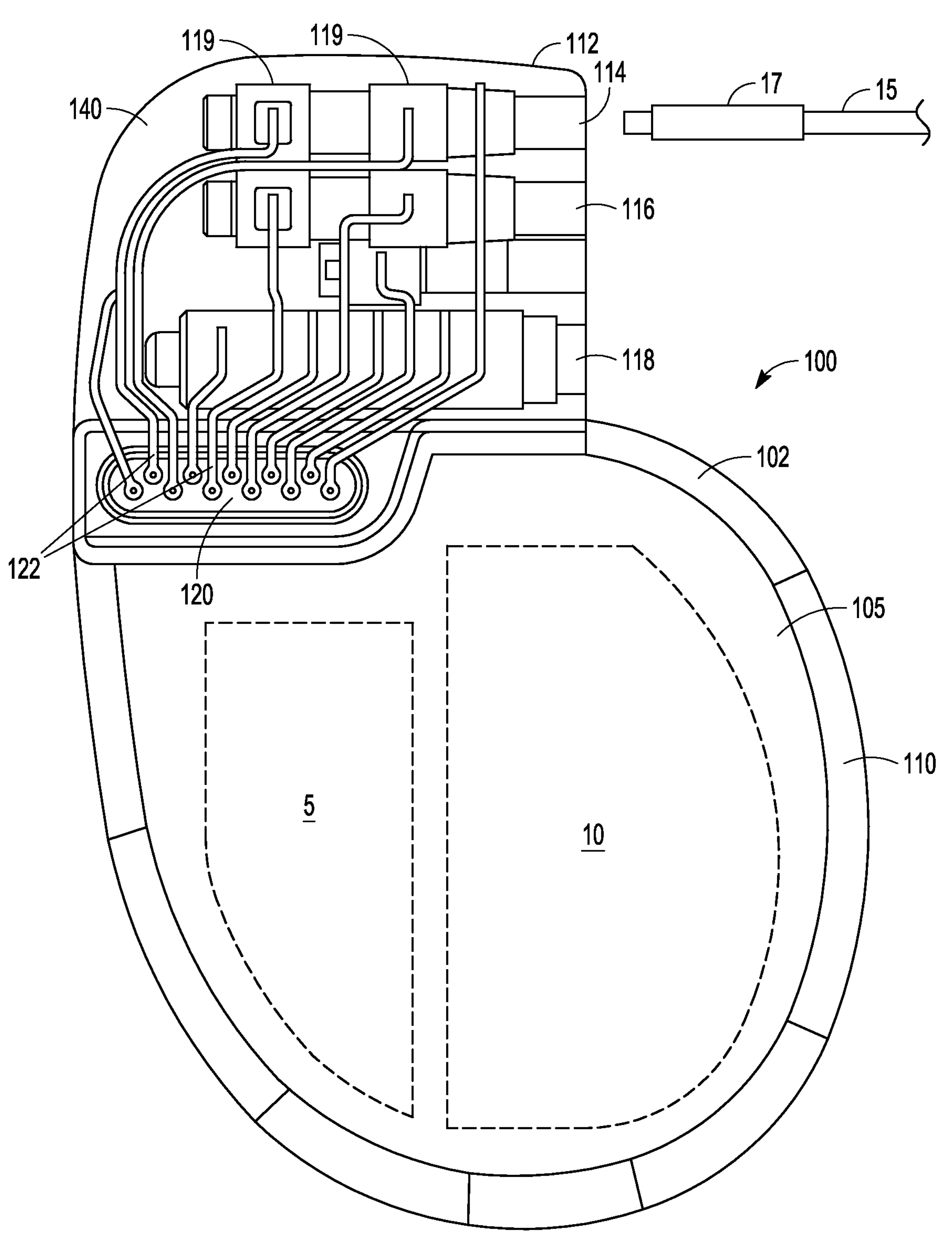
FIG. 1 shows an example implantable medical device, in accordance with one embodiment.

FIG. 1 shows an implantable system 100 including an implantable medical device 102, in accordance with one embodiment. The implantable medical device 102 includes a pulse generator 105 and at least one implantable lead 15. The pulse generator 105 includes a housing 110 and a header 112 mounted to the housing 110. The pulse generator 105 can be implanted into a subcutaneous pocket made in the wall of a patient's chest. Alternatively, the pulse generator 105 can be placed in a subcutaneous pocket made in the abdomen, or in other locations. Pulse generator 105 can include electronic devices such as a power supply 5 including a battery, a capacitor, and other components housed in the housing 110. The pulse generator 105 can further include other electronic devices such as microprocessors 10 to provide processing, evaluation, and to deliver electrical shocks and pulses of different energy levels and timing for defibrillation, cardioversion, and pacing to a heart in response to cardiac arrhythmia including fibrillation, tachycardia, heart failure, and bradycardia.

The header 112 can include one or more bores 114, 116, 118 to receive an implantable lead 15. The implantable lead 15 can include electrodes on a distal end to provide therapy to a body and include a terminal pin 17 on the proximal end to couple to the bore 114, 116, 118. At least one electrical conductor is disposed within the lead 15 and extends from the proximal end to the electrode. The electrical conductor carries electrical currents and signals between the pulse generator 105 and the electrode.

Contacts on the terminal pin 17 can electrically contact electrical contacts 119 within the bores 114, 116, 118 to allow signals and therapy to be delivered to and from the electrodes in the body to the electronics 5, 10 within the housing 110. The contacts 119 can be connected by wires 122 to a feedthrough assembly 120 to electrically communicate between the lead 15 and the electronics within the housing 110. The bores 114, 116, 118 can be overmolded by a clear plastic 140 to form the header 112.

In one example, the header 112 can be formed from a polymer material. A polymer can provide a number of desirable features, such as biocompatibility, strength, resilience, and ease of manufacturing. In one example, the header 112 is molded separately from the housing 110, and later bonded to the housing 110 using an adhesive. In a second example, the header 112 can be molded in place (overmolded) and contacts a surface of the housing 110 during a curing or hardening process.

In other embodiments, the implantable system 100 can also be suitable for use with implantable electrical stimulators, such as, but not limited to, neuro-stimulators, skeletal stimulators, central nervous system stimulators, or stimulators for the treatment of pain.

As noted, sometimes the insertion of a lead into the bore can require a large force. Accordingly, a lower friction between the lead and the bore is desirable. One method to reduce the friction is to apply an additive to the bore substrate material. However, the additive needed to provide the lower friction results in an opaque surface where the user cannot see within the bore to ascertain the location and position of the lead to determine if the lead is fully inserted into the bore. Accordingly, the present system provides a composite bore, where at least one of the bores 114, 116, 118 includes a composite structure.

Figures 2, 3:
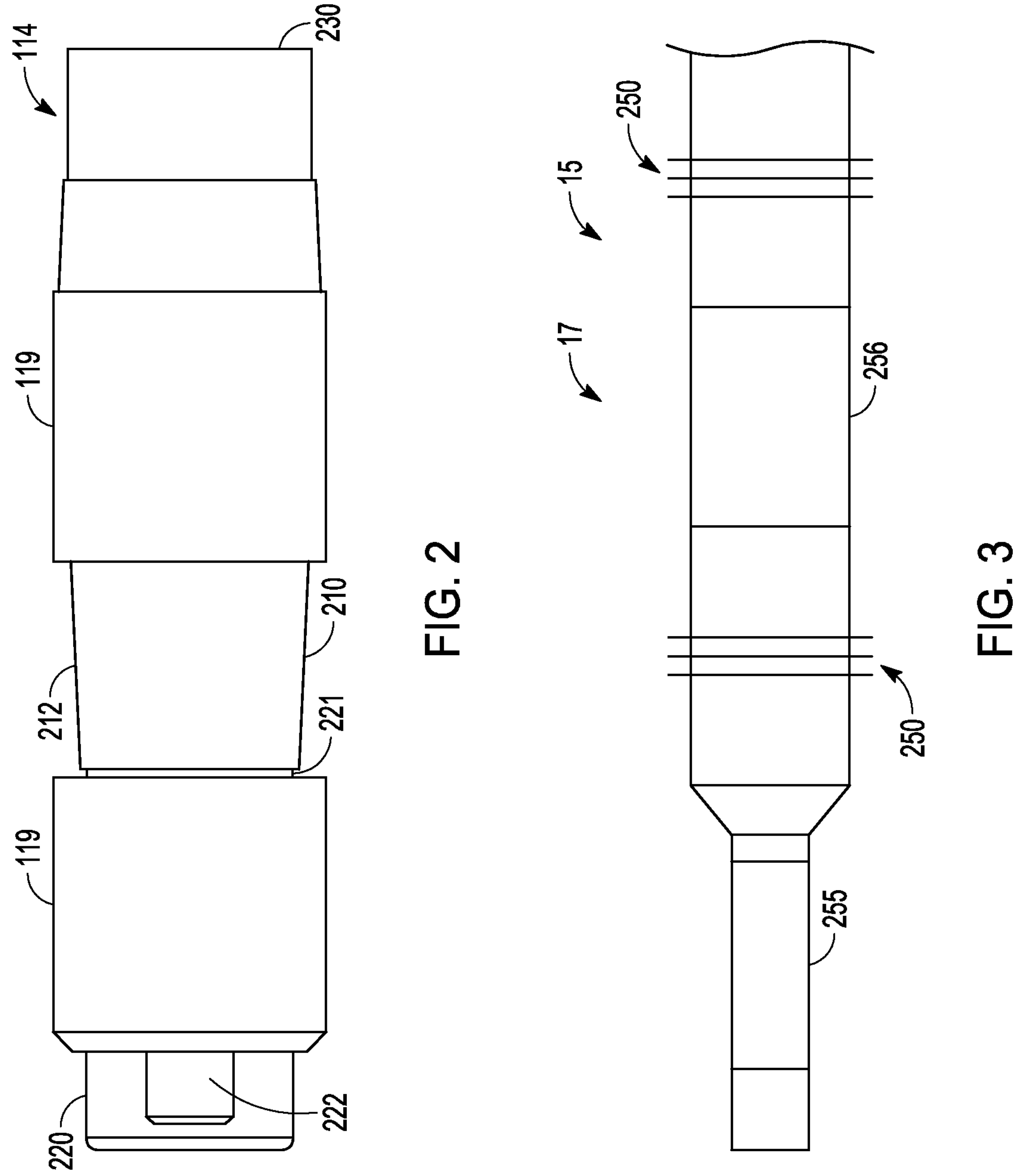
FIG. 2 shows a side view of a bore, in accordance with one embodiment.
FIG. 3 shows a side view of a lead, in accordance with one embodiment.

For example, FIG. 2 shows side view of a bore, in accordance with one embodiment. In FIG. 2, bore 114 is discussed, with the understanding that the bore could be any of bores 114, 116, 118. FIG. 3 shows a side view of the lead 15 adapted to be received by the bore 114. Here, a first section 210 of the bore 114 includes inner walls 212 having a relatively lower coefficient of friction compared to inner walls 222 of the bore 114 at a closed tip end section 220 of the bore 114.

Here, the first section 210 extends from a bore opening 230 to a beginning 221 of the closed tip end section 220. In one example, the bore 114 can define two different diameters with the first section 210 having a larger diameter than the closed tip end section 220. This matches the shape of the terminal pin 17 of the lead 15. Accordingly, the first section 210 would extend from the bore opening 230 to the beginning 221 of the smaller diameter section of the bore 114.

Accordingly, the closed tip end section 220 of the bore 114 includes the walls 222 having a relatively higher coefficient of friction compared to the walls 212 of the first section 210 of the bore 114. Thus, there is a reduced lead insertion of force for the lead 15 as the lead goes through the first section 210 of the bore 114.

In one embodiment, the walls 212 of the first section 210 of the bore 114 include an additive to a clear substrate material of the bore 114 to provide the lower coefficient of friction. The additive makes the walls 212 of the first section

Figures 4, 5:
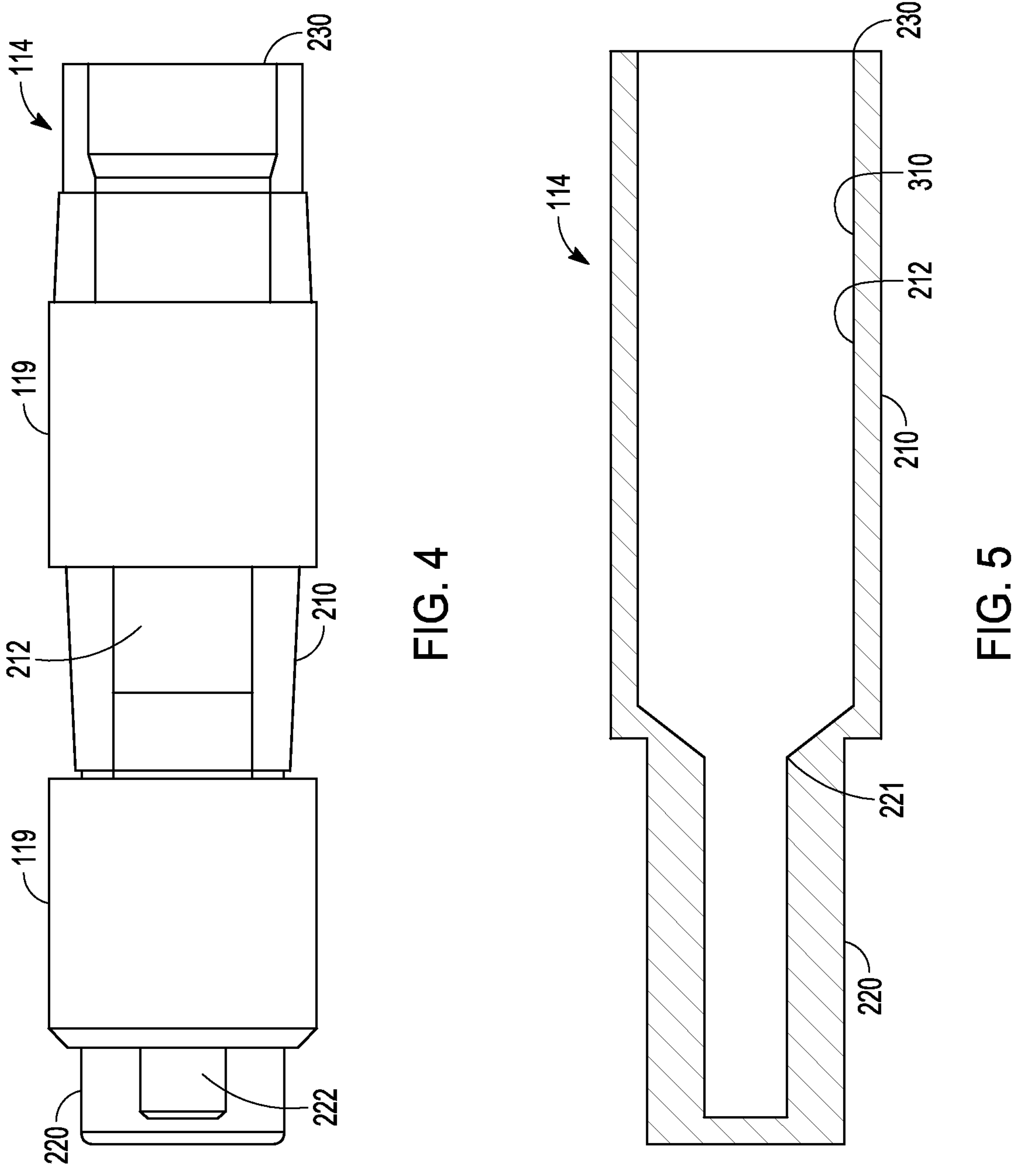
FIG. 4 shows a side view of a bore, in accordance with one embodiment.
FIG. 5 shows a cross-section view of a bore, in accordance with one embodiment.

210 opaque while the walls 222 of the closed tip end section 220 remain clear such that a user can see a lead within the closed tip end section 220 of the bore 114. (For reference, FIG. 4 shows a side view of the bore 114 without the friction reducing additive.).

As shown in FIG. 1, the bores 114, 116, 118 of the header 112 can be overmolded with a clear plastic 140. Thus, a user can see through the clear plastic of the header 112 into the clear substrate of the closed tip end section 220 of the bore 114 and see a lead being fully inserted into the bore.

Thus, the composite bore 114 uses multiple materials where the closed tip end section 220 is clear and the user can see the lead terminal pin 17 enter the closed tip end section 220 while the first section 210 (where a user doesn't need to see the lead) can have the low friction additive material added. This helps provide a low insertion force while also allowing for visual verification of the lead insertion.

In one example of forming the bore 114, the entire bore 114 can be formed of the same clear substrate with the friction reducing additive being added to the substrate only in the first section 210 to make the first section 210 have a lower coefficient of friction than the clear substrate, while also making the first section 210 opaque. The low friction additive is not added to the closed tip end section 220, thus leaving that section clear. Thus, the user can see into the closed tip end section 220 through the overmolded plastic 140 of the header 112 (FIG. 1) and see a lead 15 enter and be fully inserted into the closed tip end section 220.

In this example, there are no seals within the bore 114. Instead, one or more seals 250 can be on the lead 15 itself. For example, the lead 15 can be an IS-1 or DF-1 type implantable lead. The bore 114 can include the electrical contacts 119 to contact one or more contacts 255, 266 on the lead. Again, the bore 114 can be configured to receive an IS-1 or DF-1 type implantable lead.

FIG. 5 shows a cross-section view of the bore 114, in accordance with one embodiment. Here, a non-migrating lubricant 310 can be located on the wall 212 of the first section 210 of the bore 114 from the opening 230 to the beginning 221 of the closed tip end section 220. The non-migrating lubricant 310 has lower coefficient of friction than a substrate material of the bore 114. In one example, the non-migrating lubricant 310 can be a lubricant such as Dimethyl Polysiloxane. The lubricant 310 can be sprayed and cured onto the walls 212 of the first section 210. In one example, the lubricant 310 can make the first section 210 opaque. Thus, the lubricant is not sprayed into the closed tip end section 220 so that the user can visually see the lead terminal 17 entering the closed tip end section 220.

Figure 6:
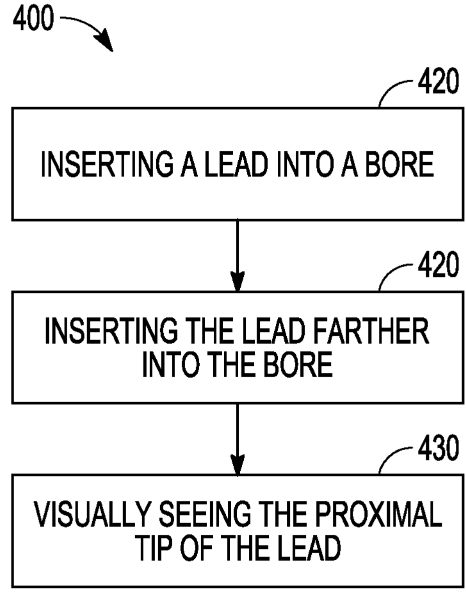
FIG. 6 shows a method for inserting the lead into a header, in accordance with one embodiment.

FIG. 6 shows a method (400) for inserting the lead into a header, in accordance with one embodiment. Method (400) can include inserting a lead into a bore (410) wherein the lead first goes through a first section of the bore having a lower coefficient of friction than a closed tip end section of the bore; inserting the lead farther into the bore (420) such that a proximal tip of the lead enters the closed tip end section; and visually seeing the proximal tip of the lead (430) within the closed tip end section.

As discussed above, the bore can include a composite structure wherein the first section of the bore includes walls having a relatively lower coefficient of friction compared to walls of the bore at the closed tip end section of the bore. Accordingly, the walls of the first section can be opaque and the walls of the closed tip end section are clear such that a user can see a lead within the closed tip end section of the bore.

In one example, the method (400) can include applying a non-migrating lubricant onto the inner walls of the first section of the bore.

Figure 7:
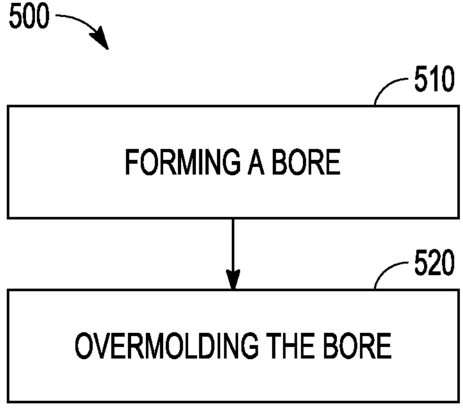
FIG. 7 shows a method of manufacturing a header for an implantable device, in accordance with one embodiment.

FIG. 7 shows a method (500) of manufacturing a header for an implantable device, in accordance with one embodiment. The method (500) can include forming a bore (510) wherein the bore includes a structure wherein a first section of the bore includes walls having a relatively lower coefficient of friction compared to walls of the bore at a closed tip end section of the bore; and overmolding the bore (520) to form a header.

As discussed, the bore can have a composite structure where the walls of the first section of the bore can include an additive to a substrate material of the bore to provide the lower coefficient of friction. The additive makes the walls of the first section opaque while the walls of the closed tip end section remain clear such that a user can see a lead within the closed tip end section of the bore. Overmolding the bore can include overmolding with a clear plastic.

The method (500) can include applying a non-migrating lubricant on the walls of the first section of the bore.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim Rather, inventive subject matter may lie in less than all features of a particular disclosed embodiment. Thus, the following claims are hereby incorporated into the Detailed Description, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. An implantable medical device comprising:

a housing including electronic devices within the housing; and a header attached to the housing and including one or more bores configured to receive a lead;

wherein one of the bores includes a structure wherein a first section of the bore includes walls having a relatively lower coefficient of friction compared to walls of the bore at a closed tip end section of the bore.

2. The implantable medical device of claim 1, wherein the walls of the first section of the bore include an additive to a substrate material of the bore to provide the lower coefficient of friction.

3. The implantable medical device of claim 2, wherein the walls of the first section are opaque and the walls of the closed tip end section are clear such that a user can see a lead within the closed tip end section of the bore.

4. The implantable medical device of claim 2, wherein the walls comprise internal surfaces of the bore, and wherein the additive makes the walls of the first section opaque while the walls of the closed tip end section remain clear to allow visual verification of lead insertion.

5. The implantable medical device of claim 1, wherein the header includes a clear plastic.

6. The implantable medical device of claim 1, wherein the entire bore is formed of the same clear substrate with an additive being added to the substrate only in the first section to make the first section have a lower coefficient of friction than the clear substrate.

7. The implantable medical device of claim 1, wherein there are no seals within the bore.

8. The implantable medical device of claim 1, wherein the bore is configured to receive an IS-1 or DF-1 type implantable lead.

9. The implantable medical device of claim 1, wherein the bore includes an electrical contact to contact a lead.

10. The implantable medical device of claim 1, wherein the first section extends from a bore opening to a beginning of the closed tip end section.

11. The implantable medical device of claim 1, wherein a non-migrating lubricant is located on the wall of the first section of the bore.

12. The implantable medical device of claim 11, wherein the non-migrating lubricant has lower coefficient of friction than a substrate of the bore.

13. The implantable medical device of claim 1, wherein the walls comprise internal surfaces of the bore, and wherein the first section of the bore has a larger diameter than the closed tip end section.

14. A method for inserting a lead into a header, the method comprising:

inserting a lead into a bore wherein the lead first goes through a first section of the bore having a lower coefficient of friction than a closed tip end section of the bore;

inserting the lead farther into the bore such that a proximal tip of the lead enters the closed tip end section; and visually seeing the proximal tip of the lead within the closed tip end section.

15. The method of claim 14, wherein the bore includes a composite structure wherein the first section of the bore includes walls having a relatively lower coefficient of friction compared to walls of the bore at the closed tip end section of the bore, and wherein the walls of the first section of the bore include an additive to a substrate material of the bore to provide the lower coefficient of friction.

16. The method of claim 15, wherein the walls of the first section are opaque and the walls of the closed tip end section are clear such that a user can see a lead within the closed tip end section of the bore, and wherein the header is overmolded with a clear plastic.

17. The method of claim 14, wherein a non-migrating lubricant is located on walls of the first section of the bore.

18. A method of manufacturing a header for an implantable device, the method comprising:

forming a bore wherein the bore includes a structure wherein a first section of the bore includes walls having a relatively lower coefficient of friction compared to walls of the bore at a closed tip end section of the bore; and overmolding the bore to form a header.

19. The method of claim 18, wherein the walls of the first section of the bore include an additive to a substrate material of the bore to provide the lower coefficient of friction, wherein the walls of the first section are opaque and the walls of the closed tip end section are clear such that a user can see a lead within the closed tip end section of the bore, and wherein the header is overmolded with a clear plastic.

20. The method of claim 18, including applying a non-migrating lubricant on the walls of the first section of the bore.

* * * * *